US008466086B2

(12) United States Patent
Carlson et al.

(10) Patent No.: US 8,466,086 B2
(45) Date of Patent: Jun. 18, 2013

(54) NUTRITIVE MEDIA AND MANUFACTURED SEEDS COMPRISING SAME

(75) Inventors: William C. Carlson, Olympia, WA (US); Jeffrey E. Hartle, Milton, WA (US); James A. Grob, Auburn, WA (US); Katherine M. Salatas, Tacoma, WA (US); Mollie K. Heilesen, Tacoma, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 939 days.

(21) Appl. No.: 10/371,612

(22) Filed: Feb. 20, 2003

(65) Prior Publication Data

US 2003/0167684 A1    Sep. 11, 2003

Related U.S. Application Data

(62) Division of application No. 09/529,933, filed as application No. PCT/US98/24820 on Nov. 20, 1998, now abandoned.

(60) Provisional application No. 60/066,232, filed on Nov. 20, 1997.

(51) Int. Cl.
*A01N 25/26* (2006.01)
*A01N 43/60* (2006.01)
*A01C 1/06* (2006.01)
*A01G 31/00* (2006.01)

(52) U.S. Cl.
USPC .............. 504/100; 504/136; 47/57.6; 47/62 N

(58) Field of Classification Search
USPC ............ 504/127, 128, 100; 47/57.6, 58.1 SE, 47/DIG. 9; 800/298
See application file for complete search history.

(56) References Cited

U.S. PATENT DOCUMENTS

| | | | |
|---|---|---|---|
| 4,583,320 A | 4/1986 | Redenbaugh | |
| 4,777,762 A | 10/1988 | Redenbaugh et al. | |
| 4,802,905 A | 2/1989 | Spector | |
| 5,036,007 A * | 7/1991 | Gupta et al. | 435/422 |
| 5,236,469 A | 8/1993 | Carlson et al. | |
| 5,427,593 A | 6/1995 | Carlson et al. | |
| 5,529,597 A | 6/1996 | Iijima | |
| 5,564,224 A | 10/1996 | Carlson et al. | |
| 5,565,355 A | 10/1996 | Smith | |
| 5,687,504 A | 11/1997 | Carlson et al. | |
| 5,701,699 A | 12/1997 | Carlson et al. | |
| 5,771,632 A | 6/1998 | Liu et al. | |
| 5,821,126 A | 10/1998 | Durzan et al. | |
| 5,840,567 A * | 11/1998 | Durzan | 435/422 |

FOREIGN PATENT DOCUMENTS

| | | |
|---|---|---|
| CA | 2208504 | 12/1994 |
| WO | WO99/26470 | 6/1999 |

OTHER PUBLICATIONS

Ball, Ernest, "Growth of the Embryo of Ginkgo Biloba Under Experimental Conditions, III. Growth Rates of Root and Shoot upon Media Absorbed Through the Cotyledons," American Journal of Botany 46(2); pp. 130-139, Feb. 1959.
Berlyn, Graeme P. and J.P. Miksche, "Growth of Excised Pine Empryos and the Role of the Cotyledons During Germination in Vitro," American Journal of Botany 52(7), pp. 730-736, 1965.
Brown, Claud L. and E. M. Gifford Jr., "The Relation of the Cotyledons to Root Development of Pine Embryos Grown in Vitro," Harvard University, Cambridge, MA, Sep. 6, 1957.
Brown, N.A.C. and J. van Staden, "Smoke as a germination cue: a review," Plant Growth Regulation 22: 115-124, Kluwer Academic Publishers, Netherlands, 1997.
Carpita, N.C. et al.; "Cold stratification and growth of radicles of loblolly pine (*Pinus taeda*) embryos," Physiol. Plant, 59: 601-606, Copenhagen, 1983.
Dodds, John H. and Lorin W. Roberts, "Experiments in Plant Tissue Culture," Cambridge University Press, pp. 21-34, 138, Cambridge, 1982.
Engvild, K.C., "Growth and Chlorophyll Formation of Dark-Grown Pine Embryos on Different Media," Physiologia Plantarum, vol. 17, pp. 867-874, 1964.
Feirer, Russell P., "15. The Biochemistry of Conifer Embryo Development: Amino Acids, Polyamines and Storage Proteins," Somatic Embryogenesis in Woody Plants, vol. 1, pp. 317-336, Kluwer Academic Publishers, Netherlands, 1995.
Gupta, Praymod K. and Don J. Durzan, "Biotechnology of Somatic Polyembryogenesis and Plantlet Regenaration in Loblolly Pine," Bio/Technology, vol. 5, pp. 147-151, Feb. 1987.
Jager, A.K. et al., "Food-flavouring smoke extracts promote seed germination," S. African Journal of Botany, vol. 62, No. 5, pp. 282-284, Oct. 1996.
Jelic, Gordana and Mita Bogdanovic, "Antagonism Between Abscisic Acid and Cytokinin in Chlorophyll Synthesis in Pine Seedlings," Plant Science, 61 pp. 197-202, Elsevier Scientific Publishes Ireland Ltd., 1988.
King, Janice E. and David J. Gifford, "Amino Acid Utilization in Seeds of Loblolly Pine during Germination and Early Seedling Growth," Plant Physiology, 113:1-11, 1997.
King, Janice E. and David J. Gifford, "Utilization of Arginine, a Key Amino Acid in Loblolly Pine During Germination and Early Seedling Growth," Session 61, Seed Physiology, Department of Biological Sciences, University of Alberta, Edmonton, AB, Plant Biology '97 Program, Aug. 1997.
Lechowski, Z. and J. Bialczyk, "Calcium mediated cytokinin action on chlorophyll synthesis in isolated embryo of Scots pine," Biologia Plantarum 35 (1): 53-62, 1993.

(Continued)

*Primary Examiner* — Alton Pryor
(74) *Attorney, Agent, or Firm* — Christensen, O'Connor, Johnson, Kindness, PLLC

(57) ABSTRACT

Manufactured seeds are disclosed that comprise a unit of totipotent plant tissue and a nutritive medium. The nutritive medium can contain a number of different components selected from the following: a gel solute, charcoal, a carbon source, urea, $KNO_3$, $NH_4NO_3$, $CuCl_2$, $CuSO_4$, KI, $KH_2PO_4$, $CaCl_2$, $MgSO_4$, $Na_2EDTA$, $FeSO_4$, ferric citrate, $MnSO_4$, $MnCl_2$, $H_3BO_3$, $ZnSO_4$, $CoCl_2$, $Na_2MoO_4$, $(NH_4)_2MoO_4$, thiamine, riboflavin, pyridoxine, HCl, Ca-pantothenate, nicotinic acid, biotin, folic acid, and myo-inositol. The nutritive medium can also include any of various protein amino acids, any of various polyamines, any of various oxygen-absorbing compounds, any of various non-protein amino acids, and/or a smoke suspension.

19 Claims, No Drawings

OTHER PUBLICATIONS

Maruyama, E. et al., "Alginate-Encapsulated Technology for the Propagation of the Tropical Forest Trees: *Cedrela odorata* L., *Guazuma crinita* MART., and *Jacaranda mimosaefolia* D. Don," Silvae Genetica 46, (1), pp. 17-23, 1997.

Mothes, K., "The Metabolism of Urea and Ureides," Canadian Journal of Botany, vol. 39, pp. 1785-1807, 1961.

Obroucheva, Natalie V., "Development of the mature root growth pattern in the course of seed germination," Structure and Function of Plant Roots, 23-27, Martinus Nijhoff/Dr. W. Junk Publishers, 1981.

Pattnaik, S.K. et al., "Efficient plant retrieval from alginate-encapsulated vegitative buds of mature mulberry trees," Scientia Horticulturae, vol. 61/3-4 227-239, Elsevier Science B.V., 1995.

Pierce, S.M. et al., "Smoke-induced germination of succulents (Mesembryanthemacceae) from fire-prone and fire-free habitats in South Africa," Oecologia (1995) 102: 520-522, Springer-Verlag 1995.

Schou, L., "On Chlorophyll Formation in the Dark in Excised Embryos of *Pinus jeffreyi*," Physiologia Plantarum, vol. 4, pp. 617-620, 1951.

Stone, Edward C., "Embryo Dormancy and Embryo Vigor of Sugar Pine ad Affected by Length of Storage and Storage Temperatures," Forest Science, vol. 3, No. 4, pp. 357-371, 1957.

Teasdale, Robert D. et al., "Mineral Nutrient Requirements of a Loblolly Pine (*Pinus taeda*) Cell Suspension Culture," Journal of Plant Physiol., vol. 82, 942-945, 1986.

Veith, Robert and Ewald Komor, "Nutrient Requirement for Optimal Growth of Sugarcane Suspension Cells: Nicotinic Acid is an Essential Growth Factor," Journal of Plant Physiol. vol. 139, pp. 175-181, 1991.

J. van Staden et al., "Interaction between a plant-derived smoke extract, light and phytohormones on the germination of light-sensitive lettuce seeds," Plant Growth Regulation 17: 213-218, Kluwer Academic Publishers, 1995.

J. van Staden et al., "The search for germination stimulants in plant-derived smoke extracts," S.-Afr. Journal of Botany, 61(5): 260-263, 1995.

Grob, J.A., et al. "Dimensional Model of Zygotic Douglas-Fir Embryo Development," *International Journal of Plant Sciences* *160*(4):653-662, 1999.

Timmis, R., "Bioprocessing for Tree Production in the Forest Industry: Conifer Somatic Embryogenesis," *Biotechnology Progress* *14*(1):156-166, Feb. 1998.

Engvild, Physiologia Plantarum, vol. 17, 1964, p. 866-874.

Brown et al., Plant Growth Regulation 22:115-124, 1997.

Mothes, Can. J. Botany, vol. 39 (1961), p. 1785-1807.

Feirer, Somatic Embryogenesis in Woody Plants, vol. 1, 317-336.

Gupta et al., Plant Cell Reports (1985) 4:177-179.

\* cited by examiner

NUTRITIVE MEDIA AND MANUFACTURED SEEDS COMPRISING SAME

RELATED APPLICATIONS

This application is a divisional application of U.S. patent application Ser. No. 09/529,933, filed Apr. 21, 2000, now abandoned, which claims the benefit under 35 U.S.C. §365(c) of PCT/US98/24820, filed Nov. 20, 1998, which claims the benefit under U.S.C. §119(e) of U.S. Provisional Patent Application Ser. No. 60/066,232, filed Nov. 20, 1997, the disclosures of all are hereby expressly incorporated by reference.

FIELD OF THE INVENTION

The invention pertains to nutritive media, methods for using such media in the production of manufactured seeds, and manufactured seeds comprising same.

BACKGROUND OF THE INVENTION

In many instances it is desirable to grow large numbers of genetically identical plants. These plants can be selected and grown based on their particular qualities, such as their ability to grow in a particular climate, or their ability to produce a particular type or quality of fiber. Unfortunately, in many cases the production of such plants through standard breeding is not feasible.

Standard plant breeding techniques are labor intensive and, because they usually involve fusion of gametes, tend to introduce genetic variability. The genetic variability is a result of crossing over of chromosomes, which often occurs during meiosis. Additionally, standard breeding techniques require that the breeder wait until a plant is mature enough to breed. In some cases, this means waiting many years. This delay decreases productivity and increases costs. Therefore, it is desirable to produce large numbers of genetically identical plants via culturing of somatic or zygotic plant embryos.

Somatic or zygotic plant embryos may be cultured in the form of "manufactured seeds". Manufactured seeds are essentially analogs of botanic seed and typically include a nutrient medium (termed here in a "nutritive medium"), and typically include structural features that serve to protect the embryo before, during, and after germination. References that describe manufactured seeds include U.S. Pat. Nos. 5,564,224; 5,687,504; and 5,701,699, all to Carlson et al. These patents disclose elements of such seeds, for instance, a manufactured seed coat, methods for using such manufactured seeds, and plant germinants produced from manufactured seeds.

A problem with manufactured seeds to date is the relatively low numbers of successful germinants from such seeds compared to botanical (natural) seeds, and relatively low numbers of "normal" germinants from manufactured seeds, i.e., viable, uniform, and commercially useful germinants. Abnormal germinants possess any of various malformations such as small and/or deformed radicals, hypocotyls, or cotyledons. Although many factors appear to cause abnormal germination, the results generally indicate that manufactured seeds, as currently known in the art, do not provide a correct balance of nutrients and other elements to the seed.

Therefore, there is a need for nutritive media that contain a suitable profile of nutrients and other elements that, when incorporated into manufactured seeds, facilitate normal and successful germination and germinant growth with normal organ development.

In order to be commercially viable, a nutritive medium desirably facilitates the germination of manufactured seeds at a rate at least similar to the germination rate of sexually produced seeds. Commercial viability can be assessed by taking into account the market size and the volume of product necessary to meet market needs. In the case of plant-related products the market is vast. Therefore, a difference in the germination rate of 10% or 20% can have an immense impact on the commercial viability of manufactured seeds.

Researchers have investigated the effects caused by the addition of various compounds to nutritive media in order to further the understanding of germination and/or growth of plant embryos on such media. For example, the effect of various nutrients on chlorophyll formation in embryos grown in the dark has been studied by Bogorad, *Botanical Gazette* 3: 221-241, 1950, and by Engvild, *Physiologia Plantarum* 17: 866-874, 1964; the effect of sucrose concentration has been studied by Schau, *Physiologia Plantarum* 4: 617-620, 1951, and by Ball, *American Journal of Botany* 46: 130-139, 1958; the effect of cytokinins on germination has been studied by Khan, *Science* 71:853-859, 1971; the effect of smoke on germination has been studied by Brown and Van Staden, *Plant Growth Regulation* 22:115-124, 1997; and the effect of amino acids as sources of organic nitrogen has been studied by Engvild (cited above).

In the laboratory, growth of plant embryos on the surface of an agar medium in a petri dish or the like is known. Unfortunately, the correlation between the germination of a plant embryo on the surface of an agar medium and the germination of an embryo from a manufactured seed is weak. This is because inter alia, there are many substantial differences between bare plant embryos and manufactured seeds. A key difference is the physical structure of the seed, which can have a profound impact on survival of the embryo inside the seed and on germination success.

There also remain large differences between manufactured seeds and corresponding natural seeds. Whereas, the embryo relies on the megagametophyte for nutrients useful for germination, the embryo in a manufactured seed relies on the nutritive medium that is provided in the manufactured seed.

Also, an agar medium used as a surface on which plant embryos are grown appears to have substantially different requirements compared to a nutritive medium for use in manufactured seed.

Therefore, there is a need for nutritive media that, when incorporated into manufactured seeds, provides an improved germination rate compared to conventional manufactured seeds.

SUMMARY OF THE INVENTION

In accordance with one aspect of the present invention, manufactured seeds are provided that comprise a unit of totipotent plant tissue and a nutritive medium. The nutritive medium preferably comprises 0 g/L to 30 g/L gel solute, 5 mM to 200 mM carbon source, 0 mM to 20 mM $KNO_3$, 2.5 mM to 5 mM $NH_4NO_3$, 0 mM to 0.01 mM KI, 0.01 mM to 20 mM $KH_2PO_4$, 0.5 mM to 5 mM $CaCl_2$, 0.1 mM to 10 mM $MgSO_4$, 0 mM to 0.1 mM $Na_2EDTA$, 0 mM to 0.1 mM $FeSO_4$, 0 mM to 0.1 mM $MnSO_4$, 0.01 mM to 1 mM $H_3BO_3$, 0.0001 mM to 0.005 mM $ZnSO_4$, 0 mM to 0.0001 mM $CoCl_2$, 0 mM to 0.0001 mM $CuSO_4$, 0 mM to 0.001 mM $Na_2MoO_4$, 0 mM to 0.01 mM thiamine-HCl, 0.001 mM to 0.005 mM pyridoxine-HCl, 0.001 mM to 0.02 mM nicotinic acid, 0.05 mM to 2.5 mM myo-inositol, and 0.002 mM to 0.2 mM L-glycine. The nutritive medium can also include any of various additional components such as one or more vitamins, charcoal, smoke suspension, and one or more carbon sources (e.g., a monosaccharide, a disaccharide, or a starch).

Any of various different amino acids can be incorporated into the nutritive medium as required. Such amino acids can be those that are commonly found incorporated into proteins (termed "protein amino acids"). The preferred protein amino acids are one or more of L-asparagine, L-glutamine, L-lysine, L-serine, L-proline, L-arginine, L-valine, L-alanine, L-cysteine, L-leucine, L-tyrosine, L-threonine, L-phenylalanine, L-histidine, L-glycine, L-tryptophan, L-isoleucine, L-methionine, and mixtures thereof.

The nutritive medium can include one or more amino acids that are not commonly found incorporated into proteins (termed "non-protein amino acids"). There are over 200 such amino acids, some of which are argininosuccinate, citrulline, canavanine, and ornithine. The non-protein amino acids also encompass the D-stereoisomers of the protein amino acids.

The nutritive medium can comprise one or more compounds involved in the metabolism of nitrogen. Representative examples of such compounds include urea and/or polyamines such as one or more of spermidine, spermine, and putrescine.

The nutritive medium can include a smoke suspension. A suitable smoke suspension contains one or more compounds generated through the process of burning organic matter such as cellulosic material.

According to another aspect of the invention, manufactured seeds are provided that comprise a modified nutritive medium. Such a medium preferably comprises 0 g/L to 30 g/L gel solute, 0 g/L to 5 g/L charcoal, 5 mM to 200 mM carbon source, 0 mM to 30 mM urea, 0 mM to 20 mM $KNO_3$, 2.5 mM to 5 mM $NH_4NO_3$, 0 mM to 0.01 mM KI, 0.01 mM to 20 mM $KH_2PO_4$, 0.5 mM to 5 mM $CaCl_2$, 0.1 mM to 10 mM $MgSO_4$, 0 to 0.1 mM $Na_2EDTA$, 0 mM to 0.1 mM $FeSO_4$, 0 mM to 0.5 mM ferric citrate, 0 mM to 0.1 mM $MnSO_4$. 0 mM to 0.1 mM $MnCl_2$, 0.01 mM to 1 mM $H_3BO_3$, 0.0001 mM to 0.005 mM $ZnSO_4$, 0 mM to 0.0001 mM $CoCl_2$, 0 mM to 0.0001 mM $CuSO_4$, 0 mM to 0.005 mM $CuCl_2$, 0 mM to 0.001 mM $Na_2MoO_4$, 0 mM to 0.001 mM $(NH_4)_2MoO_4$, 0 mM to 0.01 mM thiamine-HCl, 0 mM to 0.001 mM riboflavin, 0.001 mM to 0.005 mM pyridoxine-HCl, 0 mM to 0.04 mM Ca-pantothenate, 0.001 mM to 0.02 mM nicotinic acid, 0 mM to $1.0 \times 10^{-5}$ mM biotin, 0 mM to 0.001 mM folic acid, 0.05 mM to 2.5 mM myo-inositol, 0 mM to 2 mM L-asparagine, 0 mM to 6 mM L-glutamine, 0 mM to 2 mM L-lysine, 0 mM to 2 mM L-serine, 0 mM to 2 mM L-proline, 0 mM to 8 mM L-arginine, 0 mM to 2 mM L-valine, 0 mM to 2 mM L-alanine, 0 mM to 2 mM L-cysteine, 0 mM to 2 mM L-leucine, 0 mM to 2 mM L-tyrosine, 0 mM to 2 mM L-threonine, 0 mM to 2 mM L-phenylalanine, 0 mM to 2 mM L-histidine, 0.002 mM to 0.2 mM L-glycine, 0 mM to 2 mM L-tryptophan, 0 mM to 2 mM L-isoleucine, and 0 mM to 2 mM L-methionine. Such a nutritive medium can also include one or more additional compounds selected from any of various vitamins, hormones, a smoke suspension, and sources of carbon. For example, the modified nutritive medium can include 0 to 5 g/L charcoal and a carbon source such as a monosaccharide, a disaccharide, or a starch.

A modified nutritive medium according to the invention can include one or more compounds involved in the metabolism of nitrogen. Representative examples of such compounds are urea and polyamines such as spermidine, spermine, and putrescine.

The modified nutritive medium according to the invention can include a "smoke suspension". A suitable "smoke suspension" contains one or more compounds that are generated through the process of burning organic matter.

The modified nutritive medium can include one or more non-protein amino acids.

According to another aspect of the invention, methods are provided for germinating a unit of totipotent plant tissue. A representative embodiment of such a method comprises the steps of: providing a nutritive medium as summarized above, providing a unit of totipotent plant tissue, placing the unit of totipotent plant tissue in "functional contact" with the nutritive medium, and placing the manufactured seed in an environment conducive for plant growth so as to allow the plant tissue to grow and germinate from the manufactured seed.

The foregoing and additional features and advantages of the invention will be more readily apparent from the following detailed description.

DETAILED DESCRIPTION OF THE PREFERRED EMBODIMENT

I. Basic Nutritive Medium

A basic nutritive medium according to the invention can have a profile within one of the two ranges provided below in Table 1. The column labeled "Concentration Range 1" pertains to preferred concentration ranges of the representative components. The column labeled "Concentration Range 2" pertains to more preferred concentration ranges.

TABLE 1

BASIC MEDIUM

| Medium Component | Concentration Range 1 | Concentration Range 2 |
|---|---|---|
| gel solute | 0 g/L to 30 g/L | 10 g/L to 25 g/L |
| carbon source | 5 mM to 200 mM | 25 mM to 175 mM |
| $KNO_3$ | 0 mM to 20 mM | 10 mM to 15 mM |
| $NH_4NO_3$ | 2.5 mM to 5 mM | 2 mM to 4 mM |
| KI | 0 mM to 0.01 mM | 0.002 mM to 0.005 mM |
| $KH_2PO_4$ | 0.01 mM to 20 mM | 0.05 mM to 18 mM |
| $CaCl_2$ | 0.5 mM to 5 mM | 1 mM to 3 mM |
| $MgSO_4$ | 0.1 mM to 10 mM | 0.2 mM to 3 mM |
| $Na_2EDTA$ | 0 mM to 0.1 mM | 0.01 mM to 0.8 mM |
| $FeSO_4$ | 0 mM to 0.1 mM | 0.01 mM to 0.05 mM |
| $MnSO_4$ | 0 mM to 0.1 mM | 0.02 mM to 0.5 mM |
| $H_3BO_3$ | 0.01 mM to 1 mM | 0.1 mM to 0.5 mM |
| $ZnSO_4$ | 0.0001 mM to 0.005 mM | 0.0003 mM to 0.004 mM |
| $CoCl_2$ | 0 mM to $1 \times 10^{-4}$ Mm | $1 \times 10^{-5}$ mM to $1 \times 10^{-4}$ mM |
| $CuSO_4$ | 0 mM to $1 \times 10^{-4}$ MIA | $1 \times 10^{-5}$ mM to $1 \times 10^{-4}$ mM |
| $Na_2MoO_4$ | 0 mM to 0.001 mM | $1 \times 10^{-4}$ to 0.001 mM |
| thiamine-HCl | 0 mM to 0.01 mM | 0.001 mM to 0.005 mM |
| pyridoxine-HCl | 0.001 mM to 0.005 mM | 0.001 mM to 0.004 mM |
| nicotinic acid | 0.001 mM to 0.02 mM | 0.001 mM to 0.01 mM |
| myo-inositol | 0.05 mM to 2.5 mM | 0.1 mM to 1 mM |
| L-glycine | 0.002 mM to 0.2 mM | 0.01 mM to 0.1 mM |

In Table 1, concentrations given in g/L denote grams of the respective component per liter of medium. The basic medium preferably contains at least fifteen of the components listed in Table 1 and more preferably at least twenty of the components listed in Table 1.

The basic nutritive medium can be sterilized by autoclaving, filter sterilizing, or by using another suitable method. The nutritive medium can be incorporated into manufactured seed as described in, e.g., U.S. Pat. No. 5,701,699 to Carlson, incorporated herein by reference. The basic nutritive medium facilitates germination of seedlings from manufactured seed containing such medium.

In Table 1, certain components (e.g., thiamine) are listed as the HCl form. One of ordinary skill in the art will appreciate that the basic nutritive medium can be formulated using such components that do not contain HCl. For example, it is possible to use thiamine without the HCl instead of thiamine-HCl.

The present invention also encompasses nutritive media, derived from the basic nutritive medium described above, having an altered profile of components, including one or more added components.

Such additional components include one or more protein amino acids, one or more non-protein amino acids, charcoal, smoke suspension, one or more carbon sources, and any of various components of the metabolic pathways pertaining to nitrogen utilization by plants. Components of these pathways include, but are not limited to, urea, putrescine, spermidine, and spermine.

II. Additional Components

A. Amino Acids

Representative protein amino acids that can be added to the basic nutritive medium include one or more of the following: L-glutamine, L-arginine, L-proline, L-asparagine, L-lysine, L-serine, L-valine, L-alanine, L-cysteine, L-leucine, L-tyrosine, L-threonine, L-phenylalanine, L-histidine, L-tryptophan, L-glycine, and L-isoleucine. A preferred concentration of protein amino acids in the nutritive medium is 0 mM to 8 mM, more preferably 0.01 mM to 4 mM.

In addition to, or instead of, the protein amino acids listed above, the nutritive medium may comprise one or more amino acids that are not usually constituents of proteins. Such "non-protein" amino acids are commonly found in certain plants as storage proteins, and over 200 such non-protein amino acids are known. (As used herein, the "non-protein" amino acids include any of the D-stereoisomers of the protein amino acids.) By way of example, ornithine, canavanine, or other non-protein amino acid (or mixture thereof) can be added to the nutritive medium at a concentration of 0 mM to 3 mM, more preferably 0.1 mM to 1.25 mM per non-protein amino acid.

B. Charcoal

According to the invention charcoal can favorably influence germination when added to a nutritive medium. Preferably, the charcoal is in the form of a powder and is activated by pretreatment with HCl. Charcoal appears to facilitate increased hypocotyl length and increased radical length of germinating plant embryos of certain species of plants. In such instances the preferred concentration of charcoal is 0 g/L to 5 g/L, more preferably 2 g/L to 3 g/L.

C. Smoke Suspension

The by-products of burning organic matter can contribute to increased germination. Solutions containing these by-products can be generated by burning organic matter (e.g., wood or other cellulosic material), washing the charred material with water, and collecting the water. Solutions can also be obtained by heating the organic matter (e.g., wood or other cellulosic material), and condensing and diluting volatile substances released from such heating.

Certain types of smoke suspensions can be purchased from commercial suppliers. For example, and not intending to be limiting, Wright's Concentrated Hickory Seasoning Liquid Smoke may be purchased from B&G foods, Inc. Roseland, N.J. 07068.

A nutritive medium according to the invention comprising a smoke suspension can increase organ length and improve germination of certain plant species. Smoke suspension can be incorporated into the nutritive medium in any of various forms. For instance, smoke suspension can be incorporated as an aerosol, a powder, or as activated clay. The preferred concentration of Wright's Concentrated Hickory Seasoning Liquid Smoke liquid smoke suspension, if present, is between 0.0001 mL smoke suspension per liter of medium to 1 mL smoke suspension per liter of medium.

D. Carbon Source

In the germination of certain plant embryos (e.g., maize, sorghum, pearl millet), hydrolysis of sucrose to glucose and fructose (as representative carbon sources) precedes uptake of the carbon sources. Embryos of other crop plants appear to take up sucrose prior to hydrolysis. Therefore, depending on the species being germinated from the manufactured seed, the carbon source in a nutritive medium according to the invention can be, for example, one or more monosaccharides (as representative "simple" carbon sources). Alternatively or in addition to one or more simple carbon sources, the nutritive medium can include one or more "complex" carbon sources such as any of various disaccharides (e.g., sucrose), and any of various polysaccharides (e.g., starch). A preferred concentration of the carbon source (either as a single compound or as a mixture of compounds) in the medium is 5 mM to 200 mM, more preferably 25 mM to 175 mM.

E. Components of Pathways Involved in Nitrogen Utilization

A growing plant needs to be able to take in nitrogen and metabolically utilize it. A representative source of nitrogen is arginine. Therefore, certain compounds involved in the synthesis and degradation of arginine can be especially useful as additives to a nutritive medium according to the invention. One such compound is urea. A preferred concentration of urea is 0 mM to 30 mM. A more preferred concentration of urea, if used, is 5 mM to 20 mM.

In addition to or as an alternative to urea, any of various polyamines involved in the degradation of arginine can be added to a nutritive medium according to the invention. Suitable polyamines can be selected from the breakdown products of certain amino acids. By way of example, a preferred concentration of spermidine, putrescine, and/or spermidine is 0 mM to 0.5 mM per compound. A more preferred concentration is 0.01 mM to 0.5 mM per such compound present in the medium.

III. Modified Nutritive Medium

To facilitate further increases in germination success rate of (or a higher percentage of normal germinants from) manufactured seeds containing certain species of plant embryos and a nutritive medium according to the invention, the nutritive medium can comprise any of various additional components.

Representative modified nutritive media according to the invention can have a profile within one of the two ranges provided in Table 2, below. In Table 2, the column labeled "Concentration Range 1" pertains to preferred concentration ranges of the respective components. The column labeled "Concentration Range 2" pertains to more preferred concentration ranges.

TABLE 2

| MODIFIED MEDIUM | | |
|---|---|---|
| Medium Component | Concentration Range 1 | Concentration Range 2 |
| gel solute | 0 g/L to 30 g/L | 10 g/L to 25 g/L |
| Charcoal | 0 g/L to 5 g/L | 2 g/L to 3 g/L |
| carbon source | 5 mM to 200 mM | 25 mM to 175 mM |
| Urea | 0 mM to 30 mM | 5 mM to 20 mM |

TABLE 2-continued

MODIFIED MEDIUM

| Medium Component | Concentration Range 1 | Concentration Range 2 |
|---|---|---|
| $KNO_3$ | 0 mM to 20 mM | 10 mM to 15 mM |
| $NH_4NO_3$ | 2.5 mM to 5 mM | 2 mM to 4 mM |
| KI | 0 mM to 0.01 mM | 0.002 mM to 0.005 mM |
| $KH_2PO_4$ | 0.01 mM to 20 mM | 0.05 mM to 18 mM |
| $CaCl_2$ | 0.5 mM to 5 mM | 1 mM to 3 mM |
| $MgSO_4$ | 0.1 mM to 10 mM | 0.2 mM to 3 mM |
| $Na_2EDTA$ | 0 mM to 1 mM | 0.01 mM to 0.8 mM |
| $FeSO_4$ | 0 mM to 0.1 mM | 0.01 mM to 0.05 mM |
| ferric citrate | 0 mM to 0.5 mM | 0.1 mM to 0.4 mM |
| $MnSO_4$ | 0 mM to 0.1 mM | 0.02 mM to 0.5 mM |
| $MnCl_2$ | 0 mM to 0.1 mM | 0.01 mM to 0.05 mM |
| $H_3BO_3$ | 0.01 mM to 1 mM | 0.1 mM to 0.5 mM |
| $ZnSO_4$ | 0.0001 mM to 0.005 mM | 0.0003 mM to 0.004 mM |
| $CoCl_2$ | 0 mM to $1 \times 10^{-4}$ mM | $1 \times 10^{-5}$ mM to $1 \times 10^{-4}$ mM |
| $CuCl_2$ | 0 mM to 0.005 mM | 0.001 mM to 0.005 mM |
| $CuSO_4$ | 0 mM to $1 \times 10^{-4}$ mM | $1 \times 10^{-5}$ mM to $1 \times 10^{-4}$ mM |
| $Na_2MoO_4$ | 0 mM to 0.001 mM | $1 \times 10^{-4}$ mM to 0.001 mM |
| $(NH_4)_2MoO_4$ | 0 mM to 0.001 mM | $1 \times 10^{-4}$ to 0.001 mM |
| thiamine-HCl | 0 mM to 0.01 mM | 0.001 mM to 0.005 mM |
| Riboflavin | 0 mM to 0.001 mM | $1 \times 10^{-4}$ mM to 0.001 mM |
| pyridoxine-HCl | 0.001 mM to 0.005 mM | 0.001 mM to 0.004 mM |
| Ca-pantothenate | 0 mM to 0.04 mM | 0.0005 mM to 0.015 mM |
| nicotinic acid | 0.001 mM to 0.02 mM | 0.001 mM to 0.01 mM |
| Biotin | 0 mM to $1.0 \times 10^{-5}$ mM | $1 \times 10^{-7}$ mM to $1 \times 10^{-5}$ mM |
| folic acid | 0 mM to 0.001 mM | $1 \times 10^{-4}$ mM to $1 \times 10^{-3}$ mM |
| myo-inositol | 0.05 mM to 2.5 mM | 0.1 mM to 1 mM |
| L-asparagine | 0 mM to 2 mM | 0.01 mM to 1 mM |
| L-glutamine | 0 mM to 6 mM | 0.01 mM to 3 mM |
| L-lysine | 0 mM to 2 mM | 0.01 mM to 1 mM |
| L-serine | 0 mM to 2 mM | 0.01 mM to 1 mM |
| L-proline | 0 mM to 2 mM | 0.01 mM to 1 mM |
| L-arginine | 0 mM to 8 mM | 0.01 mM to 4 mM |
| L-valine | 0 mM to 2 mM | 0.01 mM to 1 mM |
| L-alanine | 0 mM to 2 mM | 0.01 mM to 1 mM |
| L-cysteine | 0 mM to 2 mM | 0.01 mM to 1 mM |
| L-leucine | 0 mM to 2 mM | 0.01 mM to 1 mM |
| L-tyrosine | 0 mM to 2 mM | 0.01 mM to 1 mM |
| L-threonine | 0 mM to 2 mM | 0.01 mM to 1 mM |
| L-phenylalanine | 0 mM to 2 mM | 0.01 mM to 1 mM |
| L-histidine | 0 mM to 2 mM | 0.01 mM to 1 mM |
| L-glycine | 0.002 mM to 0.2 mM | 0.01 mM to 0.1 mM |
| L-tryptophan | 0 mM to 2 mM | 0.01 mM to 1 mM |
| L-isoleucine | 0 mM to 2 mM | 0.01 mM to 1 mM |
| L-methionine | 0 mM to 2 mM | 0.01 mM to 1 mM |
| non-protein amino acid | 0 mM to 3 mM | 0.01 mM to 1.25 mM |
| smoke suspension | 0 to 10 mL/L medium | 0.1 mL/L to 1 mL/L medium |
| Polyamine | 0 mM to 0.5 mM | 0.01 mM to 0.5 mM |

In Table 2, concentrations given in g/L denote grams of the respective component per liter of medium. The modified medium preferably contains at least one of the protein amino acids listed in Table 2, and more preferably at least five of the protein amino acids listed in Table 2. In addition to the protein amino acids, the modified medium contains at least 15 of the other components (that are not protein amino acids) listed in Table 2 and more preferably at least 20 of the other components listed in Table 2.

In Table 2, a "polyamine" is any of various compounds comprising molecules having two or more amine groups, such as, but not limited to, putrescine, spermine, and spermidine.

The concentrations of individual components can be varied depending upon the species of plant embryo contained in the manufactured seed and upon the environment in which the seed is to be germinated.

IV. Plant Tissue

Plant tissue incorporated into a manufactured seed comprising a nutritive medium according to the invention is preferably totipotent. As used herein, "totipotent" refers to a capacity to grow and develop into a normal plant. Totipotent plant tissue has both the complete genetic information of a plant and the ready capacity to develop into a complete plant if cultured under favorable conditions. Totipotent plant tissue is obtainable from several areas of a plant, such as meristematic tissue and plant embryonic tissue.

Meristematic tissue is comprised of undifferentiated plant cells that divide to yield other meristematic cells as well as differentiated cells that elongate and further specialize to form structural tissues and organs of the plant. Meristematic tissue is located, for example, at the extreme tips of growing shoots or roots, in buds, and in the cambium layer of woody plants. Plant embryonic tissue can be found (in the form of a "zygotic" embryo) inside a botanic seed produced by sexual reproduction. Also, plant "somatic" embryos can be produced by culturing totipotent plant cells such as meristematic tissue under laboratory conditions in which the cells comprising the tissue are separated from one another and urged to develop into minute complete embryos. Alternatively, a process termed "cleavage polyembryonyl known in the art can be induced during natural embryo development in seed. For simplicity, totipotent plant tissue is referred to herein simply as the "embryo", unless stated otherwise.

V. Gel Solute

A nutritive medium according to the invention can include a substance that causes the medium to be a semisolid or have a congealed consistency under normal environmental condition (see Definitions below). A detailed description of various types of gel solutes can be found in U.S. Pat. No. 5,564,224 to Carlson, incorporated herein by reference.

VI. Oxygen-Absorbing Substances

U.S. Pat. No. 5,564,224, incorporated herein by reference, discloses various oxygen-absorbing substances (also termed "oxygen-carrying" substances). Such substances can be added to a nutritive medium according to the present invention to enhance both the absorption of oxygen and the retention of oxygen by the nutritive medium, thereby allowing the medium to maintain a concentration of oxygen that is higher than would otherwise be present in the medium solely from the absorption of oxygen from the atmosphere.

The amount and type of oxygen-carrying substance that is added to the medium will vary depending on the species being germinated from the manufactured seed. In some cases a nutritive medium including an oxygen-carrying substance does not facilitate improved germination compared to an otherwise identical nutritive medium lacking an oxygen-carrying substance.

VII. Preferred uses of Nutritive Medium

Nutritive media according to the invention are useful for manufacturing and germinating manufactured seeds in a variety of different contexts. As previously mentioned, the optimal concentrations of the various components can be adjusted within the respective stated ranges depending upon the species of embryo and the conditions under which the manufactured seed will be sown.

Representative methods used for making manufactured seeds including a nutritive medium are described in U.S. Pat. No. 5,701,699 to Carlson, incorporated herein by reference.

VIII. Definitions

The following terms are defined as follows:

"Unit of totipotent plant tissue" refers to the minimum mass of plant tissue that can give rise to a mature plant. For example, a single cell can mature into a plant, and is therefore, a unit of totipotent plant tissue. However, in a practical sense, a suitable unit of totipotent plant tissue comprises multiple cells (hence the term "tissue") such as in a plant embryo.

"Functional contact" is any contact of the plant tissue with the nutritive medium that allows for the flow of water and components from the nutritive medium to the unit of totipotent plant tissue. Therefore, functional contact can include actual physical contact or indirect contact resulting from, e.g., enclosing the plant tissue with a cotyledon restraint such as described in U.S. Pat. No. 5,687,504, incorporated herein by reference.

"Non-protein amino acid" is any amino acid that is not normally found as a constituent of proteins, for example, but not limited to, argininosuccinate, citrulline, homoserine, and ornithine.

"Gel solute" is a solute that, when added to the medium, causes the medium to become a semisolid or otherwise congeal. A preferred gel solute is neither cytotoxic nor substantially phytotoxic. Candidate gel solutes include, but are not limited to, the following: sodium alginate, agar, agarose, amylose, pectin, dextran, gelatin, starch, amylopectin, modified celluloses such as methylcellulose and hydroxyethylcellulose and polyacrylamide.

"Somatic embryo" is a plant embryo produced via the laboratory culturing of totipotent plant cells or by induced cleavage polyembryonyl.

"Zygotic embryo" is a plant embryo removed from a natural botanic seed of the corresponding plant.

"Germinant" is a plant embryo that has undergone sufficient growth and development to protrude from a manufactured seed, analogous to a plant embryo protruding from a natural botanic seed.

"Radicle" is that part of a plant embryo that develops into the primary root of the resulting plant.

"Cotyledon" refers generally to the first, first pair, or first whorl (depending on the plant type) of leaf-like structures on the plant embryo that function primarily to make food compounds in the seed available to the developing embryo, but in some cases act as food storage or photosynthetic structures.

"Hypocotyl" is that portion of a plant embryo or seedling located below the cotyledons but above the radicle.

"Epicotyl" is the portion of the seedling stem that is above the cotyledons.

"Hypocotyl length" pertains to the length of the hypocotyl at the time the hypocotyl was measured.

"Radicle length" pertains to the length of the radicle at the time the radicle was measured.

"Normalcy" denotes the presence of all expected parts of a plant (e.g., radicle, hypocotyl, cotyledon(s), epicotyl) at time of evaluation. In the case of gymnosperms, normalcy is characterized by the radicle having a length greater than 3 mM and no visibly discernable malformations compared to the appearance of control bare embryos grown on the surface of nutrient agar or the like.

It is important to note that, as long as all parts of an embryo have germinated, the corresponding germinant probably has the potential to become a normal seedling. There is no reason to believe that any malformations observed in the following examples below are fatal to germinants. Noting the quantity and quality of malformation is a convenient way to comparatively evaluate the various methods and means employed for making manufactured seeds. Fortunately, plant embryonic tissue is exquisitely sensitive to non-natural conditions and manifests that sensitivity in ways discernable to a trained observer.

EXAMPLE 1

Preparation of the Nutritive Medium

The basic nutritive medium and the modified nutritive medium are preferably prepared from pre-made stocks. The required amount of each stock solution (that is not heat-labile) is added to water. Non-stock chemicals (such as sucrose, charcoal, and agar) can be weighed out and added directly to the solution. After all the non-heat-labile chemicals and compounds are added, the medium is brought up to an appropriate volume and the pH is adjusted. The medium is then sterilized, e.g., by autoclaving. Pre-sterilized (e.g., by filtration) heat-labile components are added after the medium is removed from the autoclave and has cooled. The medium can additionally contain one or more antibiotics and/or antimycotics. For example, the medium can contain 0.1 mg/L $GA_{4/7}$ (available from Abbot Laboratories, North Chicago, Ill.) and/or 1 mL/L media Sigma product #A7292. Both of these products contain an antibiotic and an antimycotic. Additionally, since both products are heat-labile, they are preferably added after the medium has cooled to below 40° C.

The medium used in the following examples contained the components listed in Table 3. These particular concentrations were chosen for the purposes of consistency from one example to the next and are not intended to be limiting in any way. The medium chosen could have been any of various nutritive media within the scope of Table 1 or Table 2.

TABLE 3

SPECIFIC MEDIA USED FOR EXAMPLE PURPOSES

| Medium Component | Modified Medium | Basic Medium |
|---|---|---|
| Charcoal | 2.5 g/L | 2.5 g/L |
| pH | 5.7 | 5.7 |
| Sucrose | 146.07 mM | 58.43 g/L |
| Agar | 18 g/L | 18 g/L |
| Urea | 13.32 mM | 0 |
| $KNO_3$ | 0 | 11.57 mM |
| $NH_4NO_3$ | 3.74 mM | 2.577 mM |
| KI | 0 | 0.0025 mM |
| $KH_2PO_4$ | 13.23 mM | 0.625 mM |
| $CaCl_2$ | 1.54 mM | 1.133 mM |
| $MgSO_4$ | 1.98 mM | 0.367 mM |
| $Na_2EDTA$ | 0 | 0.05 mM |
| $FeSO_4$ | 0 | 0.027 |
| ferric citrate | 0.245 mM | 0 |
| $MnSO_4$ | 0 | 0.045 mM |
| $MnCl_2$ | 0.019 mM | 0 |
| $H_3BO_3$ | 0.162 mM | 0.05 mM |
| $ZnSO_4$ | 0 | $8.4 \times 10^{-3}$ mM |
| $CuCl_2$ | 0.0023 mM | 0 |
| $CuSO_4$ | | $3.2 \times 10^{-5}$ mM |
| $CoCl_2$ | 0 | $2.9 \times 10^{-5}$ mM |
| $Na_2MoO_4$ | 0 | $4.4 \times 10^{-4}$ mM |
| $(NH_4)_2MoO_4$ | 0.0003 mM | 0 |
| $GA_{4/7}$ | 0.1 mg/L | 0.1 mg/L |
| thiamine-HCl | 0.003 mM | 0.003 mM |
| Riboflavin | 0.0003 mM | 0 |
| Pyridoxine-HCl | 0.0012 mM | 0.0024 mM |
| Ca-pantothenate | 0.001 mM | 0 |

TABLE 3-continued

SPECIFIC MEDIA USED FOR EXAMPLE PURPOSES

| Medium Component | Modified Medium | Basic Medium |
|---|---|---|
| nicotinic acid | 0.0081 mM | 0.0041 mM |
| Biotin | $4.09 \times 10^{-6}$ mM | 0 |
| folic acid | 0.0003 mM | 0 |
| myo-inositol | 0.555 mM | 0.555 mM |
| L-asparagine | 0.8076 mM | 0 |
| L-glutamine | 1.8248 mM | 0 |
| L-lysine | 0.1624 mM | 0 |
| L-serine | 0.7613 mM | 0 |
| L-proline | 0.463 mM | 0 |
| L-arginine | 1.0471 mM | 0 |
| L-valine | 0.455 mM | 0 |
| L-alanine | 0.5983 mM | 0 |
| L-cysteine | 0.2204 mM | 0 |
| L-leucine | 0.6099 mM | 0 |
| L-tyrosine | 0.2942 mM | 0 |
| L-threonine | 0.2241 mM | 0 |
| L-phenylalanine | 0.3227 mM | 0 |
| L-histidine | 0.1721 mM | 0 |
| L-glycine | 0.71 mM | 0.027 mM |
| L-tryptophan | 0.1307 mM | 0 |
| L-isoleucine | 0.2036 mM | 0 |
| L-ornithine | 0 | 0 |
| L-methionine | 0.1789 mM | 0 |
| Pluronic F-68 | 3.6 g/L | 3.6 g/L |
| DC-200 silicone oil | 240 mL/L | 240 mL/L |

Generally, the sterilization of different components can be performed using any of various suitable techniques that can be performed at various stages in preparation. For example, a stock solution can be made that contains one or more of the components in the media. This stock solution can be sterilized before addition to the medium, or after addition to the medium. The solutions can be sterilized by filtration, exposure to UV light, autoclaving, or any other suitable means.

The sterilization principles described above can also be applied to other media additives. For example, amino acids, carbon sources, smoke suspension, or polyamines can be made into a stock solution that is filter sterilized. The resulting sterilized stock solutions can then be added to the medium after an intermediate solution containing other components has been autoclaved. On the other hand, these additives might be added directly to the medium and the medium as a whole subsequently sterilized.

EXAMPLE 2

General Description of the Process of Making Manufactured Seeds

Representative methods used for making manufacture seeds are described in U.S. Pat. Nos. 5,701,699 and 5,427,593 to Carlson, incorporated herein by reference.

After the manufactured seeds are prepared they can be sown in any of a variety of environments, such as in sand, vermiculite, sterile soil, and/or in the field (natural soil). For purposes of consistency the following examples contain data that were generated from the growth of manufactured seeds in sterile sand. For example, Cole™ sand, which is available from a variety of gardening supply stores can be used.

A suitable amount of sterile sand can be prepared by baking 2 L of sand at a temperature of 375° F. for 24 hours. The sand is then added to pre-sterilized trays and 285 mL water is added. Furrows are then formed and the box is sealed. The box containing the sand is then autoclaved for 1 hour at 121° C. and 1 atm pressure.

The manufactured seeds are then sown in the sand and allowed to germinate. Typically, the manufactured seeds are cultured under continuous light at room temperature (23° C.) for four to five weeks.

EXAMPLE 3

Addition of Charcoal to the Nutritive Medium

This example is directed to the effect of adding charcoal to the basic nutritive medium. Douglas-fir zygotic embryos were used in manufactured seed containing the basic medium. The control group included 36 manufactured seeds, and the test group included 36 manufactured seeds. Seeds of the test group contained the basic nutritive medium with the addition of 2.5 g/L charcoal. Seeds of the control group contained the basic nutritive medium without charcoal.

All seeds were germinated in sterile sand as described above. The measurements were taken 25 days after the seeds were sown. The results indicate that charcoal can have a significant beneficial effect on both hypocotyl and radicle length (see Table 4). The statistical differences were calculated using the SAS program PROC GLM (general linear models), available from Statistical Analysis Systems, Inc. Cary N.C., USA.

TABLE 4

AVERAGE SEEDLING DIMENSIONS PRODUCED FROM EACH TREATMENT

| | Normalcy | Radical Length | Hypocotyle Length | Cotyledon Length |
|---|---|---|---|---|
| Basic Medium | 58.33% | 0.5667 cm | 2.2222 cm | 1.24118 cm |
| Basic Medium + Charcoal | 86.11% | 0.9333 cm | 2.7500 cm | 1.22857 cm |

Significant differences at $\alpha=0.05$ were detected using the PROC GLM program.

However, no significant differences in cotyledon length were observed between the test and control group. Additionally, manufactured seeds of the test group showed a significant improvement in normalcy rates.

EXAMPLE 4

The Effect of Adding Amino Acids and Polyamines to the Nutritive Medium

In this example the addition of amino acids to the basic nutritive medium described in Table 3 was evaluated to determine the effect of the added amino acids on the germination of manufactured seeds containing such nutritive medium. The manufactured seeds were constructed by the methods described in Example 2. The control group consisted of manufactured seeds containing the basic medium. Test groups consisted of manufactured seeds containing the basic nutritive medium additionally comprising 0.50 mM L-glutamine, 0.125 mM L-proline, and 0.125 mM L-asparagine plus one additional test component (a different test component for each test group). The test components were 0.50 mM L-arginine, 0.50 mM ornithine, or a combination of polyamines (0.10 mM putrescine, 0.10 mM spermidine, and 0.10 mM spermine).

The manufactured seeds of all treatments (control and test groups) contained Douglas fir embryos. There were six replicates with six manufactured seeds from each treatment in each replicate. The seeds were germinated in sterile sand as described in Example 2. The seeds were allowed to germinate for 25 days after which organ length and normalcy of germinants were assessed. These results are shown in Table 5.

TABLE 5

AVERAGE SEEDLING DIMENSIONS PRODUCED FROM EACH TREATMENT

| Treatment | Normalcy % | Radical Length | Hypocotyl Length | Cotyledon Length |
|---|---|---|---|---|
| 1. Standard Medium | 65.87% | 0.67 cm | 2.20 cm | 1.42 cm |
| 2. Standard Medium + 2.5 g/L charcoal + 0.50 mM L-glutamine, 0.125 mM L-proline, 0.125 mM L-asparagine, 0.50 mM L-arginine | 77.8% | 1.19 cm | 2.71 cm | 1.53 cm |
| 3. Standard Medium + 2.5 g/L charcoal + 0.50 mM L-glutamine, 0.125 mM L-proline, 0.125 mM L-asparagine, 0.50 mM ornithine | 83.3% | 1.02 cm | 2.51 cm | 1.39 cm |
| 4. Standard Medium + 2.5 g/L charcoal + 0.50 mM L-glutamine, 0.125 mM L-proline, 0.125 mM L-asparagine, 0.10 mM putrescine, 0.10 mM spermine and 0.10 mM spermidine | 52.2% | .88 cm | 2.34 cm | 1.21 cm |

Significant differences at $\alpha=0.05$ were detected using the PROC GLM program.

The results show that the largest difference between the test groups and the control was in radicle length, and the least effect was found in cotyledon length.

EXAMPLE 5

Comparison of Loblolly Pine Zygotic Embryos Germinated from Manufactured Seeds Containing Basic Medium Versus the Modified Medium In this example the basic medium, without pluronic F-68 and DC-200 silicone oil, described in Table 3 was supplemented to bring the sucrose concentration to 50 g/L. This supplemented basic medium was then compared to the modified medium described in Table 3. The manufactured seeds were constructed containing loblolly pine embryos according to Example 1.

The study was designed as a randomized complete block. There were six blocks. Each block consisted of a germination box as described above with ten manufactured seeds of each treatment sown therein. The seeds were allowed to germinate for 34 days in sterile sand, after which the seeds were removed from the sand and the normalcy, presence or absence of an epicotyl, radical, hypocotyl, and cotyledon lengths of the resulting germinants were measured. The data is presented in Table 6.

TABLE 6

AVERAGE SEEDLING DIMENSIONS PRODUCED FROM EACH TREATMENT

| Treatment | Normalcy | Epicotyl Presence | Radical Length | Hypocotyl Length | Cotyledon Length |
|---|---|---|---|---|---|
| Modified Medium (Table 3) | 53.3% | 21.7% | 0.97 cm | 2.34 cm | 1.58 cm |
| Basic Medium (Table 3) + 50 g/L sucrose | 16.7% | 3.3% | 0.69 cm | 1.82 cm | 0.91 cm |

Significant differences at $\alpha=0.05$ were detected using the PROC GLM program.

Many differences in growth and germination were observed with manufactured seeds containing the modified nutritive medium versus manufactured seeds containing the basic nutritive medium. Manufactured seeds containing the modified nutritive medium exhibited significantly better germination, normalcy, epicotyl presence, and radical elongation than manufactured seeds containing the basic nutritive medium.

EXAMPLE 6

Comparison Douglas Fir Zygotic Embryos Germinated from Manufactured Seeds Containing Basic Medium Versus the Modified Medium In this example the two media formulations listed in Table 3 were incorporated into respective populations of manufactured seeds containing Douglas fir zygotic embryos. This was done to determine which of the two media was more effective at producing normal germination and organ elongation of such embryos from manufactured seeds. A third treatment was included to determine the effect of sucrose concentration on germination of such embryos. Manufactured seeds were constructed as described in Example 1. The study consisted of six replicate germination boxes with ten manufactured seeds/treatment/box. The seeds were allowed to germinate in sterile sand as described above for 27 days. Measurements were then taken and recorded. The data are presented in Table 7.

TABLE 7

AVERAGE SEEDLING DIMENSIONS PRODUCED FROM EACH TREATMENT

| Treatment | Normalcy | Radical Length | Hypocotyl Length | Cotyledon Length |
|---|---|---|---|---|
| 1) Medium 1 | 90.0% | 0.95 cm | 2.94 cm | 1.26 cm |
| 2) Medium 2 with 20 g/L sucrose | 80.0% | 1.20 cm | 3.52 cm | 1.61 cm |
| 3) Medium 2 with 50 g/L sucrose | 78.3% | 1.83 cm | 3.82 cm | 1.48 cm |

Significant differences at $\alpha=0.05$ were detected using the PROC GLM program.

These data indicate that the modified medium with either concentration of sucrose significantly increased organ elongation of Douglas fir germinants from manufactured seed. In comparison to the basic medium, the modified medium with 50 g/L sucrose produced the longest radicals and hypocotyls and increased cotyledon length.

EXAMPLE 7

The Addition of Liquid Smoke to Nutritive Medium

This example is directed to the effect of a nutritive medium including "liquid smoke" (as a representative smoke suspension) on the germination of manufactured seeds containing such a medium. The starting medium used was the modified medium listed in Table 3 without Pluronic F-68 and DC-200 silicone oil. To this starting medium various amounts of Wright's Concentrated Hickory Seasoning Liquid Smoke were added. (Wright's Concentrated Hickory Seasoning Liquid Smoke is available from B&G foods, Inc. Roseland, N.J. 07068). Treatment groups contained either 0.01 µL, 0.1 µL, 1 µL, 10 µL, 100 µL, 1 mL, or 10 mL of liquid smoke per 100 mL medium.

The manufactured seeds were prepared as described in Example 2, using Loblolly pine somatic embryos. The seeds were sown in germination boxes containing sterile sand as described above. The study consisted of six germination boxes and eight (30 seeds each) treatments with five seeds per treatment per box (a total of 240 manufactured seeds). After 34 days the seeds were scored for normalcy and organ elongation. Results are shown in Table 8.

TABLE 8

AVERAGE SEEDLING DIMENSIONS PRODUCED FROM EACH TREATMENT

| Milliliters of Liquid Smoke in 100 mL medium | Percent Normal | Root Length | Hypocotyl Length | Cotyledon Length | % With Epicotyl |
|---|---|---|---|---|---|
| T1: 0.01 mL (control) | 47 | 0.93 cm | 2.43 cm | 1.70 cm | 30 |
| T2: 0.01 µL | 50 | 1.43 cm | 2.32 cm | 1.74 cm | 43 |
| T3: 0.1 µL | 63 | 1.45 cm | 2.47 cm | 1.72 cm | 53 |
| T4: 1.0 µL | 77 | 1.31 cm | 2.34 cm | 1.77 cm | 53 |
| T5: 10 µL | 40 | 0.91 cm | 2.38 cm | 1.65 cm | 30 |
| T6: 0.1 mL | 53 | 1.24 cm | 2.42 cm | 1.60 cm | 27 |
| T7: 1.0 ml | 23 | 0.81 cm | 2.00 cm | 1.53 cm | 27 |
| T8: 10.0 mL | 0 | unchanged | unchanged | unchanged | 0 |
| Significant Block Difference | No | No | No | No | No |

Significant differences at α=0.05 were detected using the PROC GLM program.

The treatment group in which the nutritive medium contained 1.0 µL liquid smoke per 100 mL medium yielded the greatest response based on normalcy score (77%). Treatment with either 0.1 µL or 0.01 µL liquid smoke per 100 mL medium yielded significantly longer root length, and treatment with 0.01 µL, 0.1 µL, or 1 µL of liquid smoke per 100 mL medium yielded significantly higher percentage of germinants having an epicotyl compared to the treatment with 10.0 µL of liquid smoke per 100 mL medium. Though not significant, the treatments with 0.1 µL and 1.0 µL of Liquid Smoke per 100 mL medium yielded 43% more germinants having an epicotyl than the control in which the nutritive medium did not contain Liquid Smoke.

EXAMPLE 8

Effects of a Carbon Source on Germination of Manufactured Seeds

In this example several carbon sources were tested at various concentrations in the basic medium described in Table 3. Manufactured seeds were prepared as described in Example 1. Media formulations were based on the basic medium except that the following carbon sources and concentrations were used: Treatment 1—basic medium containing 20 g/L sucrose; Treatment 2—basic medium containing 20 g/L maltose; Treatment 3—basic medium containing 20 g/L glucose; Treatment 4—basic medium containing 10 g/L maltose; Treatment 5—basic medium containing 10 g/L glucose, and Treatment 6—basic medium containing 20 g/L honey. Stock solutions of the glucose and maltose used to prepare media used in Treatments 2-5 were filter sterilized instead of autoclaved. In this study there were six replicate germination boxes containing sterile sand with five manufactured seeds per Treatment in each box.

The results of this study showed no significant differences in normalcy among the various Treatments using SAS data analysis software (ρ=0.0772). However, more normal germinants were produced from manufactured seeds containing a higher concentration of any of the carbon sources than from manufactured seeds containing the lower concentration of the carbon sources (with the exception of honey). Significant differences were also detected in radical length (ρ=0.0001). The LSD mean separation procedure (run using the SAS data analysis software) revealed that Treatment 2 (20 g/L glucose) produced radicals significantly longer than all other Treatments except the control (Treatment 1). Ranking the treatments in order of longest to shortest radicals yielded the following: Treatment 3 produced 0.85 cm radicals; Treatment 1 produced 0.68 cm radicals; Treatment 6 produced 0.61 cm radicals; Treatment 5 produced 0.43 cm radicals; Treatment 2 produced 0.38 cm radicals; and Treatment 5 produced 0.34 cm radicals.

EXAMPLE 9

Effects of Sucrose Concentration on Germination of Manufactured Seeds Containing Loblolly Pine Zygotic Embryos In this Example various concentrations of sucrose were incorporated into the basic medium used in manufactured seeds containing loblolly pine zygotic embryos. Manufactured seeds were produced as described in Example 1. Treatment groups consisted of manufactured seeds containing the basic medium as described in Table 3 with either 40 g/L filter-sterilized sucrose or 50 g/L filter-sterilized sucrose. The manufactured seeds were sown its sterile sand in germination boxes as described in Example 1 with 10 seeds/treatment/box (total of 60 seeds/treatment). Data was collected 31 days after sowing. The results are shown in Table 9.

TABLE 9

AVERAGE SEEDLING DIMENSIONS PRODUCED FROM EACH TREATMENT

| Treatment | Normalcy | Radical Length | Hypocotyl Length | Cotyledon Length |
|---|---|---|---|---|
| 1) Mfd. Seed w/ Medium 1 + 40 cm g/L sucrose. | 38.3% | 0.40 cm | 1.95 cm | 1.01 |
| 2) Mfd. Seed w/ Medium 1 + 50 g/L sucrose. | 38.3% | 0.63 cm | 2.06 cm | 1.09 cm |

Significant differences at α=0.05 were detected using the PROC GLM program.

The results show that, for manufactured seeds containing Loblolly pine embryos, increasing the sucrose concentration does not increase normalcy of germinants but can increase organ elongation of the germinants.

Having illustrated and described the principles of the invention in multiple embodiments and examples, it will be apparent to those skilled in the art that the invention can be modified in arrangement and detail without departing from such principles. We claim all modifications coming within the spirit and scope of the following claims.

We claim:

1. A manufactured seed, comprising:
   (a) a structure containing a plant embryo; and
   (b) a nutritive medium comprising an urea concentration between about 5 mM to 30 mM, an L-arginine concentration between about 0.01 mM to 8 mM, and a thiamine-HCl concentration between about 0.001 mM to about 0.01 mM, wherein the nutritive medium is in functional contact with at least a root end of the plant embryo.

2. The manufactured seed of claim 1, wherein the urea concentration is about 5 mM to about 20 mM.

3. The manufactured seed of claim 2, wherein the L-arginine concentration is about 0.01 mM to about 4 mM.

4. The manufactured seed of claim 3, wherein the thiamine-HCl concentration is about 0.001 mM to about 0.005 mM.

5. The manufactured seed of claim 1, wherein the L-arginine concentration is about 0.01 mM to about 4 mM.

6. The manufactured seed of claim 1, wherein the thiamine-HCl concentration is about 0.001 mM to about 0.005 mM.

7. The manufactured seed of claim 1, wherein the nutritive medium further comprises charcoal.

8. The manufactured seed of claim 1, wherein the nutritive medium further comprises a non-protein amino acid.

9. The manufactured seed of claim 8, wherein the non-protein amino acid is ornithine.

10. The manufactured seed of claim 1, wherein the nutritive medium further comprises a carbon source, wherein the carbon source comprises sucrose.

11. The manufactured seed of claim 1, wherein the nutritive medium further comprises a smoke suspension.

12. The manufactured seed claim 1, wherein the nutritive medium further comprises a polyamine selected from the group consisting of putrescine, spermidine, spermine, and mixtures thereof.

13. The manufactured seed of claim 1, wherein the nutritive medium further comprises at least one component selected from the group consisting of about 0.01 mM to 0.1 mM L-glycine, 0.01 mM to 1 mM L-asparagine, 0.01 mM to 6 mM L-glutamine, 0.01 mM to 1 mM L-lysine, 0.01 mM to 1 mM L-serine, 0.01 mM to 1 mM L-proline, 0.01 mM to 1 mM L-valine, 0.01 mM to 1 mM L-alanine, 0.01 mM to 1 mM L-cysteine, 0.01 mM to 1 mM L-leucine, 0.01 mM to 1 mM L-tyrosine, 0.01 mM to 1 mM L-threonine, 0.01 mM to 1 mM L-phenylalanine, 0.01 mM to 1 mM L-histidine, 0.01 mM to 0.1 mM L-glycine, 0.01 mM to 1 mM L-tryptophan, 0.01 mM to 1 mM L-isoleucine, and 0.01 mM to 1 mM L-methionine.

14. The manufactured seed of claim 1, wherein the plant embryo is a gymnosperm plant embryo.

15. The manufactured seed of claim 14, wherein the gymnosperm plant embryo is pine.

16. A method for germinating a plant embryo, comprising placing any portion of a plant embryo in functional contact with a nutritive medium comprising about 5 mM to 30 mM urea, about 0.01 mM to 8 mM L-arginine, and about 0.001 mM to 0.01 mM thiamine-HCl in a manufactured seed.

17. The method of claim 16, wherein the nutritive medium further comprises at least one component selected from the group consisting of about 0.01 mM to 0.1 mM L-glycine, 0.01 mM to 1 mM L-asparagine, 0.01 mM to 6 mM L-glutamine, 0.01 mM to 1 mM L-lysine, 0.01 mM to 1 mM L-serine, 0.01 mM to 1 mM L-proline, 0.01 mM to 1 mM L-valine, 0.01 mM to 1 mM L-alanine, 0.01 mM to 1 mM L-cysteine, 0.01 mM to 1 mM L-leucine, 0.01 mM to 1 mM L-tyrosine, 0.01 mM to 1 mM L-threonine, 0.01 mM to 1 mM L-phenylalanine, 0.01 mM to 1 mM L-histidine, 0.01 mM to 0.1 mM L-glycine, 0.01 mM to 1 mM L-tryptophan, 0.01 mM to 1 mM L-isoleucine, and 0.01 mM to 1 mM L-methionine.

18. The method of claim 16, wherein the plant embryo is a gymnosperm plant embryo.

19. The method of claim 18, wherein the gymnosperm plant embryo is pine.

* * * * *